(12) United States Patent
Pelati et al.

(10) Patent No.: US 8,653,314 B2
(45) Date of Patent: Feb. 18, 2014

(54) METHOD FOR PROVIDING A CO-FEED IN THE COUPLING OF TOLUENE WITH A CARBON SOURCE

(75) Inventors: Joseph E. Pelati, Houston, TX (US); James R. Butler, Spicewood, TX (US); Sivadinarayana Chinta, Missouri City, TX (US)

(73) Assignee: Fina Technology, Inc., Houston, TX (US)

(*) Notice: Subject to any disclaimer, the term of this patent is extended or adjusted under 35 U.S.C. 154(b) by 103 days.

(21) Appl. No.: 13/457,503

(22) Filed: Apr. 27, 2012

(65) Prior Publication Data

US 2012/0296139 A1  Nov. 22, 2012

Related U.S. Application Data

(60) Provisional application No. 61/488,775, filed on May 22, 2011.

(51) Int. Cl.
*C07C 1/207* (2006.01)
*C07C 1/20* (2006.01)

(52) U.S. Cl.
USPC .................................. 585/437; 585/469

(58) Field of Classification Search
USPC .............................. 585/437, 469
See application file for complete search history.

(56) References Cited

U.S. PATENT DOCUMENTS

| 4,140,726 A | 2/1979 | Unland et al. |
| 4,463,204 A * | 7/1984 | Liu .............................. 585/437 |
| 4,479,024 A | 10/1984 | Bruylants et al. |
| 2009/0318743 A1 | 12/2009 | Arnold et al. |
| 2010/0041931 A1 | 2/2010 | Pelati et al. |
| 2011/0257451 A1 | 10/2011 | Thorman et al. |

* cited by examiner

*Primary Examiner* — Thuan D Dang

(57) ABSTRACT

A process for making styrene is disclosed that includes reacting toluene with a $C_1$ source and a co-feed in the presence of a catalyst in a reactor to form a first product stream comprising styrene, ethylbenzene, carbon monoxide, and hydrogen; separating the hydrogen and carbon monoxide from the first product stream to form a second stream; separating the hydrogen from the second stream to form a third stream comprising hydrogen and a fourth stream comprising carbon monoxide; wherein the fourth stream is recycled to the reactor and forms at least a portion of the co-feed.

5 Claims, 2 Drawing Sheets

METHOD FOR PROVIDING A CO-FEED IN THE COUPLING OF TOLUENE WITH A CARBON SOURCE

CROSS-REFERENCE TO RELATED APPLICATIONS

This application claims priority to U.S. Provisional Patent No. 61/488,775 filed on May 22, 2011.

FIELD

The present invention relates to a method for the production of styrene and ethylbenzene. More specifically, the invention relates to the alkylation of toluene with a carbon source (herein referred to as a $C_1$ source) such as methanol and/or formaldehyde, to produce styrene and ethylbenzene.

BACKGROUND

Styrene is a monomer used in the manufacture of many plastics. Styrene is commonly produced by making ethylbenzene, which is then dehydrogenated to produce styrene. Ethylbenzene is typically formed by one or more aromatic conversion processes involving the alkylation of benzene.

Aromatic conversion processes, which are typically carried out utilizing a molecular sieve type catalyst, are well known in the chemical processing industry. Such aromatic conversion processes include the alkylation of aromatic compounds such as benzene with ethylene to produce alkyl aromatics such as ethylbenzene. Typically an alkylation reactor, which can produce a mixture of monoalkyl and polyalkyl benzenes, will be coupled with a transalkylation reactor for the conversion of polyalkyl benzenes to monoalkyl benzenes. The transalkylation process is operated under conditions to cause disproportionation of the polyalkylated aromatic fraction, which can produce a product having an enhanced ethylbenzene content and reduced polyalkylated content. When both alkylation and transalkylation processes are used, two separate reactors, each with its own catalyst, can be employed for each of the processes.

Ethylene is obtained predominantly from the thermal cracking of hydrocarbons, such as ethane, propane, butane, or naphtha. Ethylene can also be produced and recovered from various refinery processes. Thermal cracking and separation technologies for the production of relatively pure ethylene can account for a significant portion of the total ethylbenzene production costs.

Benzene can be obtained from the hydrodealkylation of toluene that involves heating a mixture of toluene with excess hydrogen to elevated temperatures (for example 500° C. to 600° C.) in the presence of a catalyst. Under these conditions, toluene can undergo dealkylation according to the chemical equation: $C_6H_5CH_3 + H_2 \rightarrow C_6H_6 + CH_4$. This reaction requires energy input and as can be seen from the above equation, produces methane as a byproduct, which is typically separated and may be used as heating fuel for the process.

Another known process includes the alkylation of toluene to produce styrene and ethylbenzene. In this alkylation process, various aluminosilicate catalysts are utilized to react methanol and toluene to produce styrene and ethylbenzene. However, such processes have been characterized by having very low yields in addition to having very low yield to styrene and ethylbenzene.

In view of the above, it would be desirable to have a process of producing styrene and/or ethylbenzene that does not rely on thermal crackers and expensive separation technologies as a source of ethylene. It would further be desirable to avoid the process of converting toluene to benzene with its inherent expense and loss of a carbon atom to form methane. It would be desirable to produce styrene without the use of benzene and ethylene as feedstreams. It would also be desirable to produce styrene and/or ethylbenzene in one reactor without the need for separate reactors requiring additional separation steps. Furthermore, it is desirable to achieve a process having a high yield and selectivity to styrene and ethylbenzene. Even further, it is desirable to achieve a process having a high yield and selectivity to styrene such that the step of dehydrogenation of ethylbenzene to produce styrene can be reduced.

SUMMARY

An embodiment of the present invention, either by itself or with other embodiments, is a process for making styrene that includes reacting toluene with a $C_1$ source and a co-feed in the presence of a catalyst in a reactor to form a first product stream comprising styrene, ethylbenzene, carbon monoxide, and hydrogen; separating the hydrogen and carbon monoxide from the first product stream to form a second stream; separating the hydrogen from the second stream to form a third stream comprising hydrogen and a fourth stream comprising carbon monoxide; wherein the fourth stream is recycled to the reactor and forms at least a portion of the co-feed.

In an embodiment of the present invention, either by itself or with other embodiments, the $C_1$ source can be selected from the group of methanol, formaldehyde, formalin, trioxane, methylformcel, paraformaldehyde, methylal, dimethyl ether, and combinations thereof.

The toluene conversion can be at least 2%. The selectivity to styrene can be at least 15%. The selectivity to ethyl benzene can be at least 15%.

In an embodiment, either by itself or in combination with any other embodiment, the co-feed includes carbon monoxide and is simultaneously fed to the reactor with the toluene and the $C_1$ source. The co-feed can be present in amounts of 0.0001 to 50 wt % of the combined feed of the toluene, co-feed and $C_1$ source, optionally from 0.1 to 30 wt % of the combined feed of the toluene, co-feed and $C_1$ source In an embodiment, either by itself or in combination with any other embodiment, the catalyst includes at least one promoter on a support material. The promoter can be selected from the group of Co, Ce, Mo, Mn, Ti, Zr, V, Nb, K, Fe, Cs, Ga, B, P, Rb, Ag, Na, Cu, Mg, Mo, and combinations thereof. The support material can include a zeolite. The catalyst can include B and Cs supported on a zeolite.

The various embodiments of the present invention can be joined in combination with other embodiments of the invention and the listed embodiments herein are not meant to limit the invention. All combinations of embodiments of the invention are enabled, even if not given in a particular example herein.

DETAILED DESCRIPTION

Figure 1:
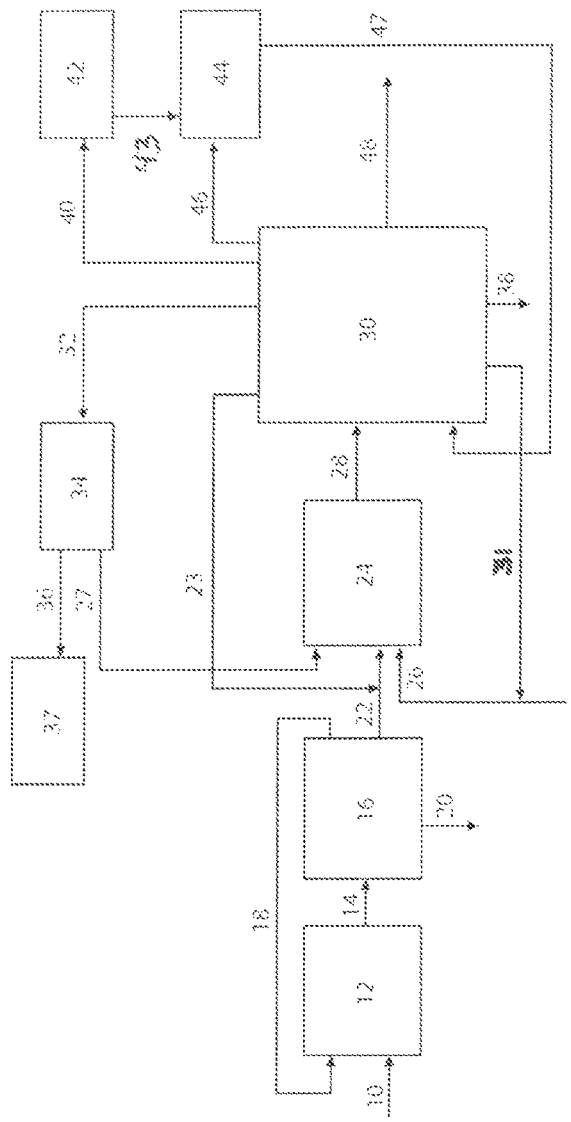
FIG. 1 illustrates a flow chart for the production of styrene by the reaction of formaldehyde and toluene, wherein the formaldehyde is first produced in a separate reactor by either the dehydrogenation or oxidation of methanol and is then reacted with toluene in the presence of a co-feed to produce styrene.

In accordance with an embodiment of the current invention, toluene is reacted with a carbon source capable of coupling with toluene to form ethylbenzene or styrene, which can be referred to as a $C_1$ source, in the presence of a co-feed to produce styrene and ethylbenzene. In an embodiment, the $C_1$ source includes methanol or formaldehyde or a mixture of the two. In an embodiment, the co-feed includes carbon monoxide (CO). In a further embodiment, the $C_1$ source is selected from the group of methanol, formaldehyde, formalin (37-50% $H_2CO$ in solution of water and methanol), trioxane (1,3,5-trioxane), methylformcel (55% $H_2CO$ in methanol), paraformaldehyde and methylal (dimethoxymethane), dimethyl ether, and combinations thereof.

Formaldehyde can be produced either by the oxidation or dehydrogenation of methanol.

In an embodiment, formaldehyde is produced by the dehydrogenation of methanol to produce formaldehyde and hydrogen gas. This reaction step produces a dry formaldehyde stream that may be preferred, as it would not require the separation of the water prior to the reaction of the formaldehyde with toluene. The dehydrogenation process is described in the equation below:

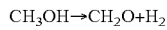

$$CH_3OH \rightarrow CH_2O + H_2$$

Formaldehyde can also be produced by the oxidation of methanol to produce formaldehyde and water. The oxidation of methanol is described in the equation below:

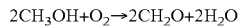

$$2CH_3OH + O_2 \rightarrow 2CH_2O + 2H_2O$$

In the case of using a separate process to obtain formaldehyde, a separation unit may then be used in order to separate the formaldehyde from the hydrogen gas or water from the formaldehyde and unreacted methanol prior to reacting the formaldehyde with toluene for the production of styrene. This separation would inhibit the hydrogenation of the formaldehyde back to methanol. Purified formaldehyde could then be sent to a styrene reactor and the unreacted methanol could be recycled.

Although the reaction has a 1:1 molar ratio of toluene and the $C_1$ source, the ratio of the $C_1$ source and toluene feedstreams is not limited within the present invention and can vary depending on operating conditions and the efficiency of the reaction system. If excess toluene or $C_1$ source is fed to the reaction zone, the unreacted portion can be subsequently separated and recycled back into the process. In one embodiment the ratio of toluene:$C_1$ source can range from between 100:1 to 1:100. In alternate embodiments the ratio of toluene:$C_1$ source can range from 50:1 to 1:50; from 20:1 to 1:20; from 10:1 to 1:10; from 5:1 to 1:5; from 2:1 to 1:2. In a specific embodiment, the ratio of toluene:$C_1$ source can range from 0.5:1 to 1.5:1.

In an embodiment, the reactants (toluene and the $C_1$ source) are combined with a co-feed. In an embodiment, the co-feed includes carbon monoxide. In another embodiment, the co-feed may be combined with nitrogen prior to combining the co-feed with the reactants. The co-feed may be combined with the reactants in any desired amounts. In an embodiment, the co-feed is added in amounts ranging from 0.0001 wt % to 50 wt % of the total feed, optionally from 0.01 wt % to 30 wt % of the total feed, optionally from 0.1 wt % to 10 wt % of the total feed, optionally from 0.1 wt % to 5 wt % of the total feed.

Turning now to the Figures, FIG. 1 illustrates a simplified flow chart of one embodiment of the styrene production process described above. In this embodiment, a first reactor (12) is either a dehydrogenation reactor or an oxidation reactor. The first reactor (12) is designed to convert the first methanol feed (10) into formaldehyde. The product stream (14) of the first reactor is then sent to a first separation unit (16) where the formaldehyde is separated from any unreacted methanol and unwanted byproducts. Any unreacted methanol (18) can then be recycled back into the first reactor (12). The unwanted byproducts (20) are separated from the formaldehyde containing stream (22).

In one embodiment, the first reactor (12) is a dehydrogenation reactor that produces formaldehyde and hydrogen and the first separation unit (16) is a membrane capable of removing hydrogen from the product stream (14).

In an alternate embodiment the first reactor (12) is an oxidative reactor that produces product stream (14) including formaldehyde and water. The product stream (14) including formaldehyde and water can then be sent to a second reactor (24) without being routed through the first separation unit (16). Optionally, the product stream can be routed to the first separation unit, wherein the water can be separated from the product stream.

As shown in FIG. 1, the formaldehyde feed stream (22) and a feed stream of toluene (26) are fed into the second reactor (24) in addition to a co-feed stream (27). The toluene (26) and formaldehyde (22) react to produce a product stream (28), which can include styrene, ethylbenzene, benzene, unreacted toluene, unreacted formaldehyde, carbon monoxide, and hydrogen. The product stream (28) of the second reactor (24) is sent to a second separation unit (30). In an embodiment, the second separation unit (30) includes one or more distillation units where the components of the product stream (28) may be separated and routed as shown in FIG. 1.

In the second separation unit (30), a mixture (32) of carbon monoxide and hydrogen is separated from the product stream (28) and sent to a third separation unit (34), wherein the carbon monoxide is separated from the hydrogen gas (36) and is routed to the second reactor (24) as the co-feed stream (27). In an embodiment, the third separation unit (34) may be a membrane capable of separating the hydrogen (36) from the carbon monoxide (27). The separated hydrogen (36) is routed from the third separation unit (34) as a hydrogen stream and, optionally, can be collected in a separate storage unit (37). There are two number 27s in FIG. 1.

As illustrated in FIG. 1, other components of the product stream (28) may be separated in the second separation unit (30). Unwanted byproducts (38), such as water, can be separated from the product stream (28). Also shown in FIG. 1, any unreacted formaldehyde (23) can be recycled back into the second reactor (24) to be reacted with the toluene (26). Any benzene (40) formed in the second reactor (24) can be separated and routed to a third reactor (42) to undergo alkylation to form ethylbenzene (43). The ethylbenzene (43) formed from the third reactor (42) can be sent to a dehydrogenation reactor (44) in addition to any ethylbenzene (46) formed in the second reactor (24), wherein the ethylbenzene will be dehydrogenated in the dehydrogenation reactor (44) producing a product stream (47) including styrene that can be fed to the second separation unit (30) for further processing. Any unreacted toluene (31) can be fed back into the second reactor (24). A styrene product stream (48) can be removed from the second separation unit (30) and subjected to further treatment or processing if desired.

The operating conditions of the reactors and separators will be system specific and can vary depending on the feedstream composition and the composition of the product streams. The second reactor (24) for the reaction of toluene and formaldehyde will operate at elevated temperatures and may contain a basic or neutral catalyst system. The temperature can range in a non-limiting example from 250° C. to 750° C., optionally from 300° C. to 500° C., optionally from 375° C. to 450° C. The pressure can range in a non-limiting example from 0.1 atm to 70 atm, optionally from 0.1 atm to 35 atm, optionally from 0.1 atm to 10 atm, optionally from 0.1 atm to 5 atm.

Figure 2:
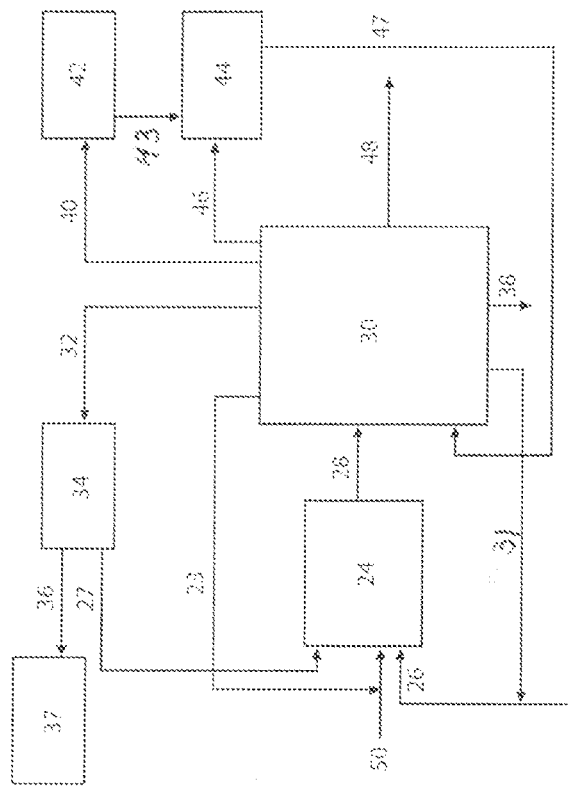
FIG. 2 illustrates a flow chart for the production of styrene by the reaction of formaldehyde and toluene, wherein methanol and toluene are fed into a reactor, wherein the methanol is converted to formaldehyde and the formaldehyde is reacted with toluene in the presence of a co-feed to produce styrene.

Looking now at FIG. 2, a simplified flow chart is shown of another embodiment of the styrene process discussed above. A feed stream containing a $C_1$ source (50) including methanol is fed along with a feed stream of toluene (26) and a co-feed stream (27) into a reactor (24). The methanol reacts with a catalyst in the reactor (24) to produce formaldehyde. The toluene and formaldehyde react in the reactor (24) to produce a product stream (28), which can include styrene, ethylbenzene, benzene, unreacted toluene, unreacted formaldehyde, carbon monoxide, and hydrogen. The product stream (28) of the reactor (24) is sent to a separation unit (30). In an embodiment, the separation unit (30) includes one or more distillation units where the components of the product stream (28) may be separated and routed as shown in FIG. 2.

In the separation unit (30), a mixture (32) of carbon monoxide and hydrogen is separated from the product stream (28) and sent to a separation unit (34), wherein the carbon monoxide is separated from the hydrogen gas (36) and is routed to the reactor (24) as the co-feed stream (27). In an embodiment, the separation unit (34) may be a membrane capable of separating the hydrogen (36) from the carbon monoxide (27). The separated hydrogen (36) is routed from the separation unit (34) as a hydrogen stream and, optionally, can be collected in a separate storage unit (37).

As illustrated in FIG. 2, other components of the product stream (28) may be separated in the separation unit (30). Unwanted byproducts (38), such as water, can be separated from the product stream (28). Also shown in FIG. 2, any unreacted formaldehyde (23) can be recycled back into the reactor (24) to be reacted with the toluene (26). Any benzene (40) formed in the reactor (24) can be separated and routed to a reactor (42) to undergo alkylation to form ethylbenzene. The ethylbenzene formed from the reactor (42) can be sent to a dehydrogenation reactor (44) in addition to any ethylbenzene (46) formed in the reactor (24), wherein the ethylbenzene will be dehydrogenated in the dehydrogenation reactor (44) producing a product stream (47) including styrene that can be fed to the separation unit (30) for further processing. Any unreacted toluene (27) can be fed back into the reactor (24). A styrene product stream (48) can be removed from the separation unit (30) and subjected to further treatment or processing if desired.

The operating conditions of the reactors and separators will be system specific and can vary depending on the feedstream composition and the composition of the product streams. The reactor (24) for the reaction of a $C_1$ source including methanol to formaldehyde and the reaction of toluene with formaldehyde will operate at elevated temperatures and may contain a basic or neutral catalyst system. The temperature can range in a non-limiting example from 250° C. to 750° C., optionally from 300° C. to 500° C., optionally from 375° C. to 450° C. The pressure can range in a non-limiting example from 0.1 atm to 70 atm, optionally from 0.1 atm to 35 atm, optionally from 0.1 atm to 10 atm, optionally from 0.1 atm to 5 atm.

Improvement in side chain alkylation selectivity may be achieved by treating a molecular sieve zeolite catalyst with chemical compounds to inhibit the external acidic sites and minimize aromatic alkylation on the ring positions. Another means of improvement of side chain alkylation selectivity can be to inhibit overly basic sites, such as for example with the addition of a boron compound. Another means of improvement of side chain alkylation selectivity can be to impose restrictions on the catalyst structure to facilitate side chain alkylation. In one embodiment the catalyst used in an embodiment of the present invention is a basic or neutral catalyst.

The catalytic reaction systems suitable for this invention can include one or more of the zeolite or amorphous materials modified for side chain alkylation selectivity. A non-limiting example can be a zeolite promoted with one or more of the following: Co, Mn, Ti, Mo, Zr, V, Nb, K, Cs, Ce, Ga, B, P, Rb, Fe, Ag, Na, Cu, Mg, or combinations thereof. In an embodiment, the zeolite can be promoted with one or more of Ce, Co, P, Cs, B, Cu, Ga, or combinations thereof. The promoter can exchange with an element within the zeolite or amorphous material and/or be attached to the zeolite or amorphous material in an occluded manner. In an embodiment the amount of promoter is determined by the amount needed to yield less than 0.5 mol % of ring alkylated products such as xylenes from a coupling reaction of toluene and a $C_1$ source.

In an embodiment, the catalyst contains greater than 0.1 wt % of at least one promoter based on the total weight of the catalyst. In another embodiment, the catalyst contains up to 30 wt % of at least one promoter. In a further embodiment, the catalyst contains from 0.1 to 10 wt % of at least one promoter. In an embodiment, the at least one promoter is boron.

Zeolite materials suitable for this invention may include silicate-based zeolites and amorphous compounds such as faujasite, mordenite, chabazite, offretite, clinoptilolite, erionite, sihealite, and the like. Silicate-based zeolites are made of alternating $SiO_2$ and $MO_x$ tetrahedra, where M is an element selected from the Groups 1 through 16 of the Periodic Table (new IUPAC). These types of zeolites have 4-, 6-, 8-, 10-, or 12-membered oxygen ring channels. An example of zeolites of this invention can include faujasites. Other suitable zeolite materials include zeolite A, zeolite L, zeolite beta, zeolite X, zeolite Y, ZSM-5, MCM-22, and MCM-41. In a more specific embodiment, the zeolite is an X-type zeolite. Alternate molecular sieves also contemplated are zeolite-like materials such as the crystalline silicoaluminophosphates (SAPO) and the aluminophosphates (ALPO).

In an embodiment, the zeolite materials suitable for this invention are characterized by silica to alumina ratio (Si/Al) of less than 1.5. In another embodiment, the zeolite materials are characterized by a Si/Al ratio ranging from 1.0 to 200, optionally from 1.0 to 100, optionally from 1.0 to 50, optionally from 1.0 to 10, optionally from 1.0 to 2.0, optionally from 1.0 to 1.5.

The present catalyst is adaptable to use in the various physical forms in which catalysts are commonly used. The catalyst of the invention may be used as a particulate material in a contact bed or as a coating material on structures having a high surface area. If desired, the catalyst can be deposited with various catalyst binder and/or support materials.

A catalyst including a substrate that supports a promoting metal or a combination of metals can be used to catalyze the reaction of hydrocarbons. The method of preparing the catalyst, pretreatment of the catalyst, and reaction conditions can influence the conversion, selectivity, and yield of the reactions.

The various elements that make up the catalyst can be derived from any suitable source, such as in their elemental form, or in compounds or coordination complexes of an organic or inorganic nature, such as carbonates, oxides, hydroxides, nitrates, acetates, chlorides, phosphates, sulfides and sulfonates. The elements and/or compounds can be prepared by any suitable method, known in the art, for the preparation of such materials.

The term "substrate" as used herein is not meant to indicate that this component is necessarily inactive, while the other metals and/or promoters are the active species. On the contrary, the substrate can be an active part of the catalyst. The term "substrate" would merely imply that the substrate makes up a significant quantity, generally 10% or more by weight, of the entire catalyst. The promoters individually can range from 0.01% to 60% by weight of the catalyst, optionally from 0.01% to 50. If more than one promoter is combined, they together generally can range from 0.01% up to 70% by weight of the catalyst. The elements of the catalyst composition can be provided from any suitable source, such as in its elemental form, as a salt, as a coordination compound, etc.

The addition of a support material to improve the catalyst physical properties is possible within the present invention. Binder material, extrusion aids or other additives can be added to the catalyst composition or the final catalyst composition can be added to a structured material that provides a support structure. For example, the final catalyst composition can include an alumina or aluminate framework as a support. Upon calcination these elements can be altered, such as through oxidation which would increase the relative content of oxygen within the final catalyst structure. The combination of the catalyst of the present invention combined with additional elements such as a binder, extrusion aid, structured material, or other additives, and their respective calcination products, are included within the scope of the invention.

The present invention is not limited by the method of catalyst preparation, and all suitable methods should be considered to fall within the scope herein. Particularly effective techniques are those utilized for the preparation of solid catalysts. Conventional methods include co-precipitation from an aqueous, an organic or a combination solution-dispersion, impregnation, dry mixing, wet mixing or the like, alone or in various combinations. In general, any method can be used which provides compositions of matter containing the prescribed components in effective amounts. According to an embodiment the substrate is charged with promoter via an incipient wetness impregnation. Other impregnation techniques such as by soaking, pore volume impregnation, or percolation can optionally be used. Alternate methods such as ion exchange, wash coat, precipitation, and gel formation can also be used. Various methods and procedures for catalyst preparation are listed in the technical report Manual of Methods and Procedures for Catalyst Characterization by J. Haber, J. H. Block and B. Dolmon, published in the International Union of Pure and Applied Chemistry, Volume 67, Nos 8/9, pp. 1257-1306, 1995, incorporated herein in its entirety.

The promoter elements can be added to or incorporated into the substrate in any appropriate form. In an embodiment, the promoter elements are added to the substrate by mechanical mixing, by incipient wetness addition, by impregnation in the form of solutions or suspensions in an appropriate liquid, or by ion exchange. In a more specific embodiment, the promoter elements are added to the substrate by impregnation in the form of solutions or suspensions in a liquid selected from the group of acetone, anhydrous (or dry) acetone, methanol, and aqueous solutions.

In another more specific embodiment, the promoter is added to the substrate by ion exchange. Ion exchange may be performed by conventional ion exchange methods in which sodium, hydrogen, or other inorganic cations that may be typically present in a substrate are at least partially replaced via a fluid solution. In an embodiment, the fluid solution can include any medium that will solubilize the cation without adversely affecting the substrate. In an embodiment, the ion exchange is performed by heating a solution containing any promoter selected from the group of Mo, Ce, Co, Mn, Ti, Zr, V, Nb, K, Cs, Ga, B, P, Rb, Fe, Ag, Na, Cu, Mg, and any combinations thereof in which the promoter(s) is(are) solubilized in the solution, which may be heated, and contacting the solution with the substrate. In another embodiment, the ion exchange includes heating a solution containing any one selected from the group of Ce, Cs, Cu, P, B, Ga, and Co and any combinations thereof. In an embodiment, the solution is heated to temperatures ranging from 50 to 120° C. In another embodiment, the solution is heated to temperatures ranging from 70 to 100° C.

The solution for use in the ion exchange method may include any fluid medium. A non-fluid ion exchange is also possible and within the scope of the present invention. In an embodiment, the solution for use in the ion exchange method includes an aqueous medium or an organic medium. In a more specific embodiment, the solution for use in the ion exchange method includes water.

The promoters may be incorporated into the substrate in any order or arrangement. In an embodiment, all of the promoters are simultaneously incorporated into the substrate. In more specific embodiment, each promoter is in an aqueous solution for ion-exchange with and/or impregnation to the substrate. In another embodiment, each promoter is in a separate aqueous solution, wherein each solution is simultaneously contacted with the substrate for ion-exchange with and/or impregnation to the substrate. In a further embodiment, each promoter is in a separate aqueous solution, wherein each solution is separately contacted with the substrate for ion-exchange with and/or impregnation to the substrate.

In an embodiment, the promoter includes boron. In an embodiment, the catalyst contains greater than 0.1 wt % boron based on the total weight of the catalyst. In another embodiment, the catalyst contains from 0.1 to 3 wt % boron.

The boron promoter can be added to the catalyst by contacting the substrate, incipient wetness, impregnation, or any other method, with any known boron source. In an embodiment, the boron source is selected from the group of boric acid, boron phosphate, methoxyboroxine, methylboroxine, and trimethoxyboroxine and combinations thereof. In another embodiment, the boron source contains boroxines. In a further embodiment, the boron source is selected from the group of methoxyboroxine, methylboroxine, and trimethoxyboroxine and combinations thereof.

In an embodiment, a substrate may be previously treated with a boron source prior to an addition of at least one promoter, wherein the promoter includes boron. In another embodiment, a boron treated zeolite may be combined with at least one promoter, wherein the at least one promoter includes boron. In a further embodiment, boron may be added to the catalyst system by adding at least one promoter containing boron as a co-feed with toluene and methanol. In an even further embodiment, boron may be added to the catalyst system by adding boroxines as a co-feed with toluene and methanol. The boroxines can include, methoxyboroxine, methylboroxine, and trimethoxyboroxine, and combinations thereof. The boron treated zeolite further combined with at least one promoter including boron may be used in preparing a supported catalyst such as extrudates and tablets.

When slurries, precipitates or the like are prepared, they may be dried, usually at a temperature sufficient to volatilize the water or other carrier, such as from 100° C. to 250° C., with or without vacuum. Irrespective of how the components are combined and irrespective of the source of the components, the dried composition is generally calcined in the presence of an oxygen-containing gas, usually at temperatures between about 300° C. and about 900° C. for from 1 to 24 hours. The calcination can be in an oxygen-containing atmosphere, or alternately in a reducing or inert atmosphere.

The prepared catalyst can be ground, pressed, sieved, extruded, shaped and/or otherwise processed into a form suitable for loading into a reactor. The reactor can be any type known in the art to make catalyst particles, such as a fixed bed, fluidized bed, or swing bed reactor. Optionally an inert material can be used to support the catalyst bed and to place the catalyst within the bed. Depending on the catalyst, a pretreatment of the catalyst may, or may not, be necessary. For the pretreatment, the reactor can be heated to elevated temperatures, such as 200° C. to 900° C. with an air flow, such as 100 mL/min, and held at these conditions for a length of time, such as 1 to 3 hours. Then, the reactor can be brought to the operating temperature of the reactor, for example 300° C. to 550° C., or optionally down to any desired temperature, for instance down to ambient temperature to remain under a purge until it is ready to be put in service. The reactor can be kept under an inert purge, such as under a nitrogen or helium purge.

Embodiments of reactors that can be used with the present invention can include, by non-limiting examples: fixed bed reactors; fluid bed reactors; and entrained bed reactors. Reactors capable of the elevated temperature and pressure as described herein, and capable of enabling contact of the reactants with the catalyst, can be considered within the scope of the present invention. Embodiments of the particular reactor system may be determined based on the particular design conditions and throughput, as by one of ordinary skill in the art, and are not meant to be limiting on the scope of the present invention. An example of a suitable reactor can be a fluid bed reactor having catalyst regeneration capabilities. This type of reactor system employing a riser can be modified as needed, for example by insulating or heating the riser if thermal input is needed, or by jacketing the riser with cooling water if thermal dissipation is required. These designs can also be used to replace catalyst while the process is in operation, by withdrawing catalyst from the regeneration vessel from an exit line or adding new catalyst into the system while in operation.

In another embodiment, the one or more reactors may include one or more catalyst beds. In the event of multiple beds, an inert material layer can separate each bed. The inert material can include any type of inert substance. In an embodiment, a reactor includes between 1 and 25 catalyst beds. In a further embodiment, a reactor includes between 2 and 10 catalyst beds. In a further embodiment, a reactor includes between 2 and 5 catalyst beds. In addition, the co-feed, the $C_1$ source and/or toluene may be injected into a catalyst bed, an inert material layer, or both. In a further embodiment, at least a portion of the $C_1$ source and at least a portion of the co-feed are injected into a catalyst bed(s) and at least a portion of the toluene feed is injected into an inert material layer(s).

In an alternate embodiment, the entire $C_1$ source is injected into a catalyst bed(s), all of the toluene feed is injected into an inert material layer(s) and all of the co-feed is injected into one of: the catalyst bed(s), the inert material layer(s), or any combination thereof. In another embodiment, at least a portion of the toluene feed is injected into a catalyst bed(s), at least a portion of the co-feed is injected into a catalyst bed(s), and at least a portion the $C_1$ source is injected into an inert material layer(s). In a further embodiment, all of the toluene feed is injected into the first catalyst bed and a portion of the $C_1$ source and co-feed are injected into the catalyst beds along the reactor to control the toluene:C1 ratio in each catalyst bed.

The toluene and $C_1$ source coupling reaction may have a toluene conversion percent greater than 0.01 mol %. In an embodiment the toluene and $C_1$ source coupling reaction is capable of having a toluene conversion percent in the range of from 0.05 mol % to 40 mol %. In a further embodiment the toluene and $C_1$ source coupling reaction is capable of having a toluene conversion in the range of from 2 mol % to 40 mol %, optionally from 5 mol % to 35 mol %, optionally from 10 mol % to 30 mol %.

In an embodiment the toluene and $C_1$ source coupling reaction is capable of selectivity to styrene greater than 1 mol %, optionally greater than 15 mol %. In another embodiment, the toluene and $C_1$ source coupling reaction is capable of selectivity to styrene in the range of from 1 mol % to 99 mol %. In an embodiment the toluene to a $C_1$ source coupling reaction is capable of selectivity to ethylbenzene greater than 1 mol %, optionally greater than 15 mol %. In another embodiment, the toluene and $C_1$ source coupling reaction is capable of selectivity to ethylbenzene in the range of from 1 mol % to 99 mol %. In an embodiment the toluene and $C_1$ source coupling reaction is capable of yielding less than 0.5 mol % of ring alkylated products such as xylenes.

The term "conversion" refers to the percentage of reactant (e.g. toluene) that undergoes a chemical reaction.

$$\% X_{Tol}=\text{percent conversion of toluene(mol \%)}=100\times (Tol_{in}-Tol_{out})/Tol_{in}$$

The term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process.

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

The term "regenerated catalyst" refers to a catalyst that has regained enough activity to be efficient in a specified process. Such efficiency is determined by individual process parameters.

The term "selectivity" refers to the relative activity of a catalyst in reference to a particular compound in a mixture. Selectivity is quantified as the proportion of a particular product relative to all other products.

$$S_{Sty}=\text{selectivity of toluene to styrene(mol \%)}=Sty_{out}/Tol_{converted}$$

$$S_{EB}=\text{selectivity of toluene to ethylbenzene(mol \%)}=EB_{out}/Tol_{converted}$$

The term "zeolite" refers to a molecular sieve containing an aluminosilicate lattice, usually in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves. Of particular interest are the faujasites. Two types of faujasites are X-zeolite and Y-zeolite.

The various embodiments of the present invention can be joined in combination with other embodiments of the invention and the listed embodiments herein are not meant to limit the invention. All combinations of various embodiments of the invention are enabled, even if not given in a particular example herein.

While illustrative embodiments have been depicted and described, modifications thereof can be made by one skilled in the art without departing from the spirit and scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.).

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Also, it is within the scope of this disclosure that the embodiments disclosed herein are usable and combinable with every other embodiment disclosed herein, and consequently, this disclosure is enabling for any and all combinations of the embodiments disclosed herein. Other and further embodiments, versions and examples of the invention may be devised without departing from the basic scope thereof and the scope thereof is determined by the claims that follow.

What is claimed is:

1. A method of making styrene, comprising:

reacting toluene with a $C_1$ source and a co-feed in the presence of a catalyst in a reactor to form a first product stream comprising styrene, ethylbenzene, carbon monoxide, and hydrogen;

separating the hydrogen and carbon monoxide from the first product stream to form a second stream;

separating the hydrogen from the second stream to form a third stream comprising hydrogen and a fourth stream comprising carbon monoxide;

wherein the fourth stream is recycled to the reactor and forms at least a portion of the co-feed;

wherein the $C_1$ source is selected from the group consisting of methanol, formaldehyde, formalin, trioxane, methylformcel, paraformaldehyde, methylal, dimethyl ether, and combinations thereof;

wherein the catalyst comprises at least one promoter on a support material comprising a zeolite;

wherein the at least one promoter is selected from the group consisting of Ce, Cu, P, Co, Cs, Ga, and B and combinations thereof.

2. The method of claim 1, wherein the co-feed is present in amounts of 0.1 to 50 wt % of the combined feed of the toluene, co-feed and $C_1$ source.

3. The method of claim 1, having a toluene conversion of at least 2%.

4. The method of claim 1, having a selectivity to styrene of at least 15%.

5. The method of claim 1, having a selectivity to ethylbenzene of at least 15%.

* * * * *